(12) United States Patent
Kim et al.

(10) Patent No.: US 10,717,697 B2
(45) Date of Patent: Jul. 21, 2020

(54) METHOD FOR PREPARING 1,3-CYCLOHEXANEDICARBOXYLIC ACID

(71) Applicant: LOTTE CHEMICAL CORPORATION, Seoul (KR)

(72) Inventors: Sung Min Kim, Daejeon (KR); Mi Sun Cha, Daejeon (KR); Seong Hwan Choi, Daejeon (KR); Young Heon Choi, Daejeon (KR); Sung Joon Park, Daejeon (KR); Chan Yeong Yun, Daejeon (KR); Young Jong Seo, Daejeon (KR)

(73) Assignee: LOTTE CHEMICAL CORPORATION, Seoul (KR)

( * ) Notice: Subject to any disclaimer, the term of this patent is extended or adjusted under 35 U.S.C. 154(b) by 0 days.

(21) Appl. No.: 16/337,910

(22) PCT Filed: Sep. 27, 2017

(86) PCT No.: PCT/KR2017/010731
§ 371 (c)(1),
(2) Date: Mar. 28, 2019

(87) PCT Pub. No.: WO2018/062854
PCT Pub. Date: Apr. 5, 2018

(65) Prior Publication Data
US 2019/0225568 A1 Jul. 25, 2019

(30) Foreign Application Priority Data

Sep. 29, 2016 (KR) .................. 10-2016-0125868

(51) Int. Cl.
| | | |
|---|---|---|
| *C07C 51/38* | (2006.01) | |
| *B01J 23/89* | (2006.01) | |
| *C07C 51/50* | (2006.01) | |
| *C07C 51/36* | (2006.01) | |
| *B01J 21/08* | (2006.01) | |
| *B01J 35/10* | (2006.01) | |
| *C07C 61/09* | (2006.01) | |

(52) U.S. Cl.
CPC ............... *C07C 51/38* (2013.01); *B01J 21/08* (2013.01); *B01J 23/89* (2013.01); *B01J 35/10* (2013.01); *C07C 51/36* (2013.01); *C07C 51/50* (2013.01); *C07C 61/09* (2013.01)

(58) Field of Classification Search
CPC .. B01J 21/08; B01J 23/89; B01J 35/10; C07C 51/36; C07C 51/38; C07C 51/50; C07C 61/09
See application file for complete search history.

(56) References Cited

U.S. PATENT DOCUMENTS

2002/0019559 A1* 2/2002 Brunner .................. C07C 51/36
560/55

FOREIGN PATENT DOCUMENTS

| CN | 106496017 A | | 3/2017 |
|---|---|---|---|
| JP | H06-192146 A | | 7/1994 |
| JP | 2001-526252 A | | 12/2001 |
| JP | 2002-69016 A | | 3/2002 |
| JP | 2014-181199 | * | 9/2014 |
| JP | 2014-181199 A | | 9/2014 |
| JP | 2015-192958 A | | 11/2015 |
| KR | 2001-0033257 | * | 4/2001 |
| KR | 2001-0033257 A | | 4/2001 |
| KR | 10-0460371 | | 12/2004 |
| KR | 10-2014-0023912 A | | 2/2014 |
| WO | WO 99/32427 | | 7/1999 |
| WO | WO 00/78701 A1 | | 12/2000 |

OTHER PUBLICATIONS

JP 2014-181199 translation (Year: 2014).*
International Search Report and Written Opinion of the International Searching Authority, corresponding to PCT/KR2017/010731, dated Jan. 31, 2018, 14 pages.
Leon Y Leon, C. A. et al., "Adsorption and catalytic properties of Pd/SiO$_2$, Cu/SiO$_2$, and Pd-Cu/SiO$_2$ Systems: III. Carbon monoxide and benzene hydrogenation over Pd-Cu/SiO$_2$ catalysts", Applied Catalysis, 1991 vol. 69, No. 1, pp. 305-321.
Tang, et al., "RuPd Alloy Nanoparticles Supported on N-Doped Carbon as an Efficient and Stable Catalyst for Benzoic Acid Hydrogenation", ACS Catalysis, vol. 5, No. 5, 2015 (pp. 3100-3107).
Extended European Search Report for corresponding European Application No. 17856740.0, Extended European Search Report dated Apr. 3, 2020 (5 pgs.).

* cited by examiner

*Primary Examiner* — Jafar F Parsa
*Assistant Examiner* — Blaine G Doletski
(74) *Attorney, Agent, or Firm* — Lewis Roca Rothgerber Christie LLP

(57) ABSTRACT

The present invention relates to a method for preparing 1,3-cyclohexanedicarboxylic acid capable of exhibiting excellent activity, of enhancing the reaction efficiency and economic efficiency by using a catalyst having improved durability under the reaction conditions of high temperature and strong acid, of achieving excellent conversion rates by allowing most of reactants to participate in the reaction, and of obtaining products having high purity while minimizing by-products within a shorter period of time. The method for preparing 1,3-cyclohexanedicarboxylic acid may include: reducing isophthalic acid in the presence of a metal catalyst fixed to a silica support and containing a palladium (Pd) compound and a copper (Cu) compound in a weight ratio of 1:0.1 to 0.5.

14 Claims, No Drawings

METHOD FOR PREPARING 1,3-CYCLOHEXANEDICARBOXYLIC ACID

CROSS-REFERENCE TO RELATED APPLICATION

The present application is a U.S. National Phase Patent Application and claims priority to and the benefit of International Application Number PCT/KR2017/010731, filed on Sep. 27, 2017, which claims priority of Korean Patent Application Number 10-2016-0125868, filed on Sep. 29, 2016, the entire contents of all of which are incorporated herein by reference.

FIELD

The present invention relates to a method for preparing 1,3-cyclohexanedicarboxylic acid. More specifically, the present invention relates to a method for preparing 1,3-cyclohexanedicarboxylic acid capable of exhibiting excellent activity, of enhancing the reaction efficiency and economic efficiency by using a catalyst having improved durability under the reaction conditions of high temperature and strong acid, of achieving excellent conversion rates by allowing most of reactants to participate in the reaction, and of obtaining products having high purity while minimizing by-products within a shorter period of time.

BACKGROUND ART

When a compound having a carboxyl group is dissolved in a solvent phase containing water for reaction, it has acidic conditions of various intensities due to dissociation of hydrogen atoms. In particular, in the case of molecules containing two or more carboxylic acid functional groups such as dicarboxylic acid, the acidity of the solution may be higher depending on the type of molecule. As the temperature is raised for the reaction, the intensity of the acid will form a very strongly acidic conditions of pH=1 or less.

In particular, for the hydrogenation of aromatic ring compounds, a high temperature of 150 to 300° C. is essentially required. It is obvious that the pH of the acidic aqueous solution decreases in proportion to the temperature. Therefore, for the aromatic ring hydrogenation of isophthalic acid, which is an aromatic compound, it is necessary to use a catalyst having acid resistance not only at high temperature but also strongly acidic condition (pH=1 or less), thereby producing 1,3-cyclohexane dicarboxylic acid which is industrially economical.

Conventionally, there are many catalyst systems using palladium, but there were no cases applied to the aromatic ring hydrogenation of isophthalic acid. Even if it was used for the hydrogenation reaction of other organic compounds, any method for maintaining medium- to long-term activity under high temperature-strong acid conditions has not been suggested.

Therefore, there is a need to develop a new manufacturing process technology that can replace the conventionally known process for producing 1,3-cyclohexanedicarboxylic acid.

DETAILED DESCRIPTION OF THE INVENTION

Technical Problem

An object of the present invention is intended to provide a method for preparing 1,3-cyclohexanedicarboxylic acid capable of exhibiting excellent activity, of enhancing the reaction efficiency and economic efficiency by using a catalyst having improved durability under the reaction conditions of high temperature and strong acid, of achieving excellent conversion rates by allowing most of reactants to participate in the reaction, and of obtaining products having high purity while minimizing by-products within a shorter period of time.

Technical Solution

In order to achieve the above object, the present invention provides a method for preparing 1,3-cyclohexanedicarboxylic acid including a step of reducing isophthalic acid in the presence of a metal catalyst fixed to a silica support and containing a palladium (Pd) compound and a copper (Cu) compound in a weight ratio of 1:0.1 to 0.5.

Hereinafter, a method for preparing 1,3-cyclohexanedicarboxylic acid according to a specific embodiment of the present invention will be described in detail.

According to one embodiment of the invention, there can be provided a method for preparing 1,3-cyclohexanedicarboxylic acid including a step of reducing isophthalic acid in the presence of a metal catalyst fixed to a silica support and containing a palladium (Pd) compound and a copper (Cu) compound in a weight ratio of 1:0.1 to 0.5.

The present inventors have conducted studies on a method for synthesizing cycloalkane dicarboxylic acid by direct hydrogenation reaction of an aromatic dicarboxylic acid, and have found through experiments that when a metal catalyst fixed to a specific support and satisfying a weight ratio between specific active components is used, high-purity 1,3-cyclohexanedicarboxylic acid can be prepared with a high conversion rate through a simplified process as compared with a conventional process, thereby completing the present invention.

Specifically, as the preparation method of the one embodiment described above uses a metal catalyst containing a palladium (Pd) compound and a copper (Cu) compound in a specific weight ratio, the activity of the catalyst is maintained even if the reduction step of isophthalic acid is repeated twice or more while reusing the catalyst that has undergone the step of reducing isophthalic acid. Therefore, the durability of the catalyst, particularly the acid resistance, can be improved under the reduction reaction conditions of isophthalic acid to such an extent that an excellent conversion rate higher than a proper level can be realized.

In the reactor internal solution formed under the above reaction conditions, a strongly acidic condition of pH 1 or less is formed. A strongly acidic solution formed by the hydrogen dissociation of isophthalic acid, a reactant, and 1,3-cyclohexane dicarboxylic acid, a product, acts as a direct or indirect cause of inactivation of the palladium compounds, thus accelerating inactivation.

However, it is considered that in the metal catalyst used in the one embodiment, as a copper (Cu) compound as a cocatalyst is mixed together with a palladium (Pd) compound as an active component which serves to convert an aromatic dicarboxylic acid into a cycloalkane dicarboxylic acid, the copper (Cu) compound plays a role in enhancing a bonding force between the palladium (Pd) compound and the support, thus achieving excellent acid resistance even under strong acid conditions.

In addition, when isophthalic acid is reduced using a metal catalyst fixed to a silica support and containing palladium (Pd) compound and copper (Cu) compound in a specific weight ratio, almost all of the isophthalic acid, which is a reactant, can participate in the reaction to achieve a high conversion rate, and thus, it is possible to provide 1,3-cyclohexanedicarboxylic acid having high purity while minimizing by-products within a shorter period of time.

In particular, in the preparation method of one embodiment, the metal catalyst is used in a state in which the active components thereof are fixed to a specific silica support. As the active components are fixed to the silica support, it is possible to achieve the result that a high reaction conversion rate of 90% or more is secured and also the selectivity of 1,3-cyclohexanedicarboxylic acid in the finally prepared product is secured by 89% or more. These effects are considered to be attributed to the influence of a smooth reaction according to the pore characteristics of the silica support, and the like.

Further, according to the method for preparing 1,3-cyclohexanedicarboxylic acid according to one embodiment, the generation of by-products is minimal during the synthesis of 1,3-cyclohexanedicarboxylic acid from isophthalic acid, and thereby, additional process or step for separating and recovering the by-products may be omitted, and a purification process for increasing purity can be minimized. Furthermore, the method for preparing 1,3-cyclohexanedicarboxylic acid according to one embodiment allows a design of a relatively simplified reaction process and can provide high-purity 1,3-cyclohexanedicarboxylic acid in a high yield within a shorter period of time, thereby improving the efficiency and economy of the entire preparation process.

Specifically, the method for preparing 1,3-cyclohexanedicarboxylic acid according to one embodiment may include a step of reducing isophthalic acid in the presence of a metal catalyst fixed to a silica support and containing a palladium (Pd) compound and a copper (Cu) compound in a weight ratio of 1:0.1 to 0.5.

As the metal catalyst, a palladium (Pd) compound and a copper (Cu) compound may be used as active components, and the active components may be fixed to a silica support. A method for preparing the metal catalyst described above is not particularly limited, and may be carried out by a supporting method commonly used when supporting a catalytically-active metal on a porous support in the technical field to which the present invention belongs.

For example, the metal catalyst may be prepared by an impregnation method, and more specifically, it may be prepared by a method in which a palladium compound and a copper compound are dissolved in an aqueous solution to prepare a mixed metal salt, which is then impregnated into a support in a dry state, and the support impregnated with the mixed metal salt solution is dried and then calcined in air.

The drying step may be carried out at 80° C. to 150° C. under a normal pressure for 1 hour to 48 hours, and a drying method such as vacuum drying or normal pressure hot air drying can be applied.

The calcination step may be performed in the presence of a mixed gas containing oxygen, and the support was calcined at a temperature of 300° C. to 600° C. for 1 to 6 hours and cooled to normal temperature, and finally, the catalyst can be obtained.

Specifically, the silica support contained in the metal catalyst may have a specific surface area of 100 $m^2/g$ to 500 $m^2/g$. Examples of the method of measuring the specific surface area are not particularly limited, and for example, a BET measurement method may be used.

When the specific surface area of the silica support is too small, the active sites of the reactant and the catalyst are reduced, so that the reaction may not smoothly proceed, or the metal, which plays an important role in the catalyst, may not be properly supported on the support, and thus, a phenomenon in which pores are clogged or broken may occur. Also, when the specific surface area of the silica support is too large, the degree of dispersion of the catalyst metal may be excessively increased, and thus, the reaction may not rather proceed smoothly.

The total pore volume of the silica support contained in the metal catalyst may be 0.5 $cm^3/g$ to 2 $cm^3/g$. Examples of the method for measuring a pore volume are not particularly limited, and for example, a BET measurement method may be used.

When the total pore volume of the silica support contained in metal catalyst is too large, the reaction rate of the reactant and the catalyst may be excessively accelerated, so that remaining reaction byproducts may be generated in an excessive amount or dispersion of the metal as the active component is not sufficiently performed. Consequently, the contact efficiency of the reactant and the catalyst may greatly decrease, and thus, the reaction may not rather proceed smoothly.

The average pore diameter of the silica support contained in the metal catalyst may be 80 Å to 200 Å. The average pore diameter refers to an average value of diameters with respect to the pores having various diameters contained in the silica support.

The silica support may include at least one compound selected from the group consisting of silica, silica-alumina, and silica-magnesia.

In addition, the water content of the silica support may be 0.1% to 10% by weight. The 'water content' of the support is defined as a percentage of the weight of water contained in the support with respect to the total weight of the support. The silica support before supporting the catalyst can naturally absorb moisture at the humidity of the average climatic conditions to contain moisture in an amount of 10% by weight or less. When the water content of the silica support is too high, the volume of the supporting solution for dissolving metal components may be reduced, and when the catalyst is prepared at an excessively high concentration, the degree of dispersion may decrease, and also, the silica support may be used with the water content reduced as needed through a separate drying step. However, applying a separate drying step may be omitted or added from an economic point of view with respect to the cost of catalyst preparation.

The silica support contained in the metal catalyst may be prepared by various methods, and its structure and shape may be varied. However, by way of example, a silica support produced by an extrusion molding method may be used, and the silica support is a cylindrical type and may have a diameter of 1 to 3 mm, a length of 0.5 to 10 mm, and a bulk density of 0.2 to 1.2 g/ml. In this way, as the silica support is used as a support for supporting the active components in the metal catalyst, it is possible to have a technical advantage that a catalyst having improved durability under strong acid conditions can be produced. In the case of a zeolite support, there may be a disadvantage that an aluminum component structurally contained therein may be eluted to cause the disintegration of a micropore structure, and the eluted aluminum component may cause a side reaction in the reaction system or may act as an unnecessary substance in a separation and purification step. In the case of an activated carbon support, there are disadvantages in that a high-temperature heat treatment process cannot be applied due to its characteristics, and that since the binding force with the metal active component is relatively weak, it is highly likely that the active components are separated and lost.

Meanwhile, the palladium (Pd) compound contained in the metal catalyst appears to play a role in converting aromatic dicarboxylic acid to cycloalkane dicarboxylic acid and the copper (Cu) compound appears to play a role in enhancing the bonding force between the palladium (Pd) compound and the support.

When isophthalic acid is reduced in the presence of the metal catalyst, a reaction product including 1,3-cyclohexanedicarboxylic acid may be formed.

The metal catalyst may include a palladium (Pd) compound and a copper (Cu) compound in a weight ratio of 1:0.1 to 0.5, or in a weight ratio of 1:0.3 to 0.5. More specifically, the metal catalyst may include a palladium (Pd) contained in the palladium (Pd) compound and a copper (Cu) contained in the copper (Cu) compound in a weight ratio of 1:0.1 to 0.5, or in a weight ratio of 1:0.3 to 0.5.

Further, according to the molar ratio between the palladium (Pd) compound and the copper (Cu) compound, the ratio of the number of moles of the copper (Cu) compound to the number of moles of the palladium (Pd) compound may be 0.1 to 10, or 0.5 to 5.

As confirmed in Examples and the like to be described later, by using the metal catalyst containing a palladium (Pd) compound and a copper (Cu) compound in a specific weight ratio, a high conversion rate may be achieved by allowing almost all of isophthalic acid used as a reactant to participate in the reaction, and the selectivity of 1,3-cyclohexanedicarboxylic acid in the finally prepared reaction product may be highly maintained. In particular, the activity of the catalyst is maintained even if the reduction step of isophthalic acid is repeated twice or more while reusing the catalyst that has undergone the step of reducing isophthalic acid. Therefore, the durability of the catalyst can be improved under the reduction reaction conditions of isophthalic acid to such an extent that an excellent conversion rate higher than a proper level can be realized.

If the content of the copper (Cu) compound is too low relative to the palladium (Pd) compound in the metal catalyst, it is difficult to sufficiently maintain the durability of the catalyst under the reduction reaction conditions of high temperature and strongly acidic isophthalic acid. When the reduction step of isophthalic acid is repeated twice or more while reusing the catalyst that has undergone the step of reducing isophthalic acid, the activity of the catalyst decreases and thereby, the conversion rate can be greatly reduced.

In addition, if the content of the copper (Cu) compound is too high relative to the palladium (Pd) compound in the metal catalyst, there may be problems that the active component is not sufficiently dispersed in the preparation process of catalyst and the reduction step of isophthalic acid, the calcination phenomenon is accelerated and the active surface area decreases and the conversion rate may remarkedly decrease.

The palladium (Pd) compound means palladium metal itself, an organic salt of palladium or an inorganic salt of palladium. The same also applies to the copper (Cu) compound. Specifically, examples of the palladium compound and the copper compound include a complex or an ionic compound which is easily soluble in an aqueous solution, and through the process of calcinating in air in the catalyst production process, anions or ligands other than metal elements are thermally decomposed and the metal element may be bonded with oxygen to be present as a metal element in an oxide form or in a reduced form.

More specifically, examples of the palladium compound include palladium (II) nitrate ($Pd(NO_3)_2$), palladium (II) chloride ($PdCl_2$), palladium(II) acetate ($Pd(OAc)_2$), or a hydrate thereof, etc. Examples of the copper compound include copper (II) nitrate ($Cu(NO_3)_2$), copper(II) chloride ($CuCl_2$), copper(II) acetate ($Cu(OAc)_2$) or a hydrate thereof, etc.

The metal catalyst may include 0.1% to 10% by weight of the palladium (Pd) compound with respect to the silica support. The content of the copper (Cu) compound in the metal catalyst may be determined as the content of the palladium (Pd) compound and the weight ratio between the metal compounds. For example; the content of the copper (Cu) compound may be 0.01% to 10% by weight with respect to the silica support.

Meanwhile, in the step of reducing the isophthalic acid, various reduction methods may be used, and for example, the reduction method may include contacting the isophthalic acid with hydrogen gas.

In the step of reducing isophthalic acid, a method, reaction conditions; and an apparatus known to be used in a reduction reaction of aromatic carboxylic acid may be used without particular limitation, and, for example, the step of reducing isophthalic acid may be carried out at a temperature of 50° C. to 350° C., or 150° C. to 300° C. under a pressure of 30 bar to 150 bar, or 50 to 120 bar.

Specifically, the step of reducing isophthalic acid may be carried out by including converting the inside of a reactor in which the metal catalyst and the isophthalic acid are present; into the atmosphere of inert gas, followed by introducing hydrogen gas and raising the internal temperature.

That is, the step of reducing isophthalic acid may include mixing the metal catalyst and the 1,3-cyclohexanedicarboxylic acid in the inside of a reactor under an atmosphere of inert gas; introducing hydrogen gas into the reactor; and raising the temperature of the reactor to carry out a reduction reaction.

The inert gas means including not only the gas components of Group 18 on the periodic table, but also other gases which do not directly affect the hydrogenation reaction, such as nitrogen gas.

In the step of reducing isophthalic acid, the metal catalyst may be used in an amount of 10 to 80 parts by weight relative to 100 parts by weight of the isophthalic acid, in the reaction system in which isophthalic acid as a reactant, the metal catalyst, and a reaction solvent are mixed. More specifically, the addition amount of isophthalic acid in the reaction system may be 1% to 50% by weight, and the metal catalyst may be added in an amount of 0.1% to 5% by weight.

When the content or the used amount of the metal catalyst relative to the isophthalic acid is too small, the efficiency of the reduction reaction may be reduced, or the selectivity of 1,3-cyclohexanedicarboxylic acid in the finally prepared reaction product may be reduced. When the content of the catalyst is less than the above range, the production efficiency of the reaction apparatus may be reduced, and when the final product is obtained and then separated/recovered; the degradation in efficiency of the apparatus or the energy consumption may be excessive.

Further, when the content or the used amount of the metal catalyst relative to the isophthalic acid is too high, by-products are generated in an excessive amount during the progress of the reaction, and thus, in order to remove the by-products, a multi-step process must be additionally carried out, which is uneconomical, and the purity of the finally prepared product may be reduced.

Meanwhile, in the method for preparing 1,3-cyclohexanedicarboxylic acid, by carrying out the direct reduction reaction using 3-cyclohexanedicarboxylic acid as a reactant, the process may be quickly completed in a single step, and since two or more multi-step processes are not carried out, the process efficiency such as productivity and economic efficiency may be improved.

In step of reducing the isophthalic acid, the reactant itself can also undergo a direct reduction reaction, and a reduction reaction may occur in a state in which the reactant is present in a solvent phase.

Examples of the usable solvent are not particularly limited, and, for example, water or an organic solvent may be used. As an example of the organic solvent, aliphatic alcohols such as methanol, ethanol, propanol, and cyclohexanol, aliphatic hydrocarbons, such as hexane and cyclohexane, ethers such as diethyl ether and tetrahydrofuran, or a mixture of two or more thereof may be used.

Considering the effect on the separation and purification process after reaction, the solvent price, the wastewater treatment cost, and the possibility of environmental problems, the use of ion exchange water is most preferred.

The amount of the organic solvent used is not particularly limited, and, for example, the organic solvent may be used in an amount of 10% to 1,000% relative to the weight of isophthalic acid which is a reactant.

The method for preparing 1,3-cyclohexanedicarboxylic acid of one embodiment may further include separating the catalyst and then purifying the reaction product at the time of the completion of the reduction reaction process. A method that can be used for the purification is not particularly limited, but the separation and purification may be carried out by distillation, extraction, and chromatography methods.

Meanwhile, the method for preparing 1,3-cyclohexanedicarboxylic acid according to one embodiment may have a selectivity defined by the following Equation 1 of 90% or more, or 93% or more, or 90% to 100%, or 93% to 100%.

Selectivity (%)=[(Amount of 1,3-cyclohexanedicarboxylic acid (mol %)/Amount (mol %) of product)*100]  Equation 1

It can be seen that as the selectivity according to Equation 1 is higher, a large number of targeted 1,3-cyclohexanedicarboxylic acid is produced in the reaction product, and it can be confirmed that the process for preparing 1,3-cyclohexanedicarboxylic acid according to the one embodiment satisfies high selectivity and thus has excellent reaction efficiency.

Meanwhile, in the method for preparing 1,3-cyclohexanedicarboxylic acid according to one embodiment, after a step of reducing isophthalic acid in the presence of a metal catalyst fixed to a silica support and containing a palladium (Pd) compound and a copper (Cu) compound in a weight ratio of 1:0.1 to 0.5, the method may further include 4 a step of recovering the metal catalyst; and a step of reducing the isophthalic acid in the presence of the recovered metal catalyst. In this way, as the catalyst used in the reaction is reused, the amount of the catalyst used can be reduced and thus the economic efficiency of the reaction can be improved.

Specifically, in the step of recovering the metal catalyst, examples of a specific method for recovering the metal catalyst are not particularly limited, and for example, a method of filtering a metal catalyst from a reaction system containing a metal catalyst and then evaporating and drying the filtered metal catalyst may be used. The specific method of filtration or evaporation and drying is not particularly limited, and various known methods can be applied without limitation.

Further, the step of reducing isophthalic acid in the presence of the recovered metal catalyst may directly include the contents relating to the silica support, isophthalic acid and the reduction of isophthalic acid described in the above-mentioned one embodiment, except that the recovered metal catalyst is used instead of a novel metal catalyst.

Meanwhile, the step of recovering the metal catalyst; and the step of reducing isophthalic acid in the presence of the recovered metal catalyst can be repeatedly carried out twice or more. As described above, in the metal catalyst, as a copper (Cu) compound as a cocatalyst is mixed together with a palladium (Pd) compound as an active component which serves to convert an aromatic dicarboxylic acid into a cycloalkane dicarboxylic acid, the copper (Cu) compound can enhance a bonding force between the palladium (Pd) compound and the support, thus improving the durability of the catalyst.

Accordingly, even if the catalyst is reused repeatedly over a long period of time under the conditions of high temperature and strong acidic isophthalic acid reduction, the active component of the catalyst can be stably fixed to the silica support and thus exhibit excellent activity.

As the ratio of the content of the palladium (Pd) compound contained in the recovered metal catalyst to the content of the palladium (Pd) compound contained in the metal catalyst satisfies the above-described range, even if the metal catalyst is reused repeatedly over a long period of time under the conditions of high temperature and strongly acidic isophthalic acid reduction reaction, the palladium (Pd) compound, which is an active component of the catalyst, can be stably fixed on the silica support and thus exhibits excellent reaction activity.

More specifically, in the step of reducing isophthalic acid in the presence of the recovered metal catalyst, the conversion rate defined by the following Equation 2 may be 45% or more, or 45% to 80%.

Conversion rate (%)=[(Amount of 1,3-cyclohexanedicarboxylic acid added (mol %))−(Amount of 1,3-cyclohexanedicarboxylic acid remaining after reaction (mol %))]/[Amount of 1,3-cyclohexanedicarboxylic acid added (mol %)]*100.  Equation 2

The recovered metal catalyst corresponds to a catalyst which is recovered and reused after participating in the isophthalic acid reduction reaction at least once or twice.

Advantageous Effects

According to the present invention, there may be provided a method for preparing 1,3-cyclohexanedicarboxylic acid capable of exhibiting excellent activity, of enhancing the reaction efficiency and economic efficiency by using a catalyst having improved durability under the reaction conditions of high temperature and strong acid, of achieving excellent conversion rates by allowing most of reactants to participate in the reaction, and of obtaining products having high purity while minimizing by-products within a shorter period of time.

DETAILED DESCRIPTION OF THE EMBODIMENTS

The present invention will be described in more detail by way of Examples shown below. However, these Examples are given for illustrative purposes only, and the scope of the invention is not intended to be limited to or by these Examples.

Preparation Examples 1 to 3: Preparation of Metal Catalyst

Preparation Example 1

Palladium(II) nitrate dihydrate ($Pd(NO_3)_2 \cdot 2H_2O$) and copper nitrate trihydrate ($CuNO_3 \cdot 3H_2O$) were dissolved in ion-exchanged water to prepare a metal precursor solution. The metal precursor solution was dropped by the inner pore volume of the silica support [specific surface area: about 255 $m^2/g$, total pore volume: 1.03 $cm^3/g$, average pore diameter: 110 Å] to support the catalyst, which was then dried at 110° C. for 24 hours. Thereafter, the catalyst was calcined at 500° C. under an air condition to obtain a catalyst in which palladium and copper were supported in the form of a composite metal. (The weight ratio of palladium (Pd) and copper (Cu) is as shown in Table 1 below).

Preparation Example 2

A metal catalyst was prepared in the same manner as in Preparation Example 1, except that the weight ratio of palladium (Pd) and copper (Cu) was changed as shown in Table 1 below.

Preparation Example 3

A metal catalyst was prepared in the same manner as in Preparation Example 1, except that the weight ratio of palladium (Pd) and copper (Cu) was changed as shown in Table 1 below.

Examples 1 to 3: Preparation of 1,3-Cyclohexanedicarboxylic Acid

Example 1

The metal-supported catalyst obtained in Preparation Example 1, isophthalic acid, and ion-exchange water were charged into a 500 ml high-pressure reactor equipped with a stirrer so as to satisfy the weight ratios shown in Table 1 below. After replacing the atmosphere in the high-pressure reactor with nitrogen at room temperature, the temperature inside the high-pressure reactor was raised to 230° C. while introducing hydrogen gas into the high-pressure reactor, thereby carrying out hydrogenation reaction under a pressure of 80 bar. At this time, the stirring speed in the high-pressure reactor was fixed to 350 rpm and the reaction was carried out for 80 minutes. When the reaction time was reached, the inside of the reactor was cooled to room temperature, and filtered to collect a reaction product. Water was removed from the collected reaction product by distillation using a rotary evaporator to obtain 1,3-cyclohexanedicarboxylic acid as a final product.

Example 2

1,3-cyclohexanedicarboxylic acid was prepared in the same manner as in Example 1, except that 15 wt % of isophthalic acid was used as shown in Table 1 below.

Example 3

The metal catalyst used in Example 2 was filtered and then reused to prepare 1,3-cyclohexanedicarboxylic acid in the same manner as in Example 2. Subsequently, the same procedure was repeated.

Comparative Examples 1 to 4: Preparation of 1,3-Cyclohexanedicarboxylic Acid

Comparative Example 1

1,3-cyclohexanedicarboxylic acid was prepared in the same manner as in Example 1, except that the metal-supported catalyst obtained in Preparation Example 2 was charged.

Comparative Example 2

1,3-cyclohexanedicarboxylic acid was prepared in the same manner as in Example 1, except that the metal-supported catalyst obtained in Preparation Example 3 was used.

Comparative Example 3

1,3-cyclohexanedicarboxylic acid was prepared in the same manner as in Example 2, except that the metal-supported catalyst obtained in Preparation Example 2 was used.

Comparative Example 4

The metal catalyst used in Comparative Example 3 was filtered and then reused to prepare 1,3-cyclohexanedicarboxylic acid in the same manner as in Comparative Example 3. Subsequently, the same procedure was repeated.

Experimental Example: Measurement of Physical Properties of 1,3-Cyclohexanedicarboxylic Acid Obtained in Examples and Comparative Examples The physical properties of 1,3-cyclohexanedicarboxylic acid obtained in the above Examples and Comparative Examples were measured by the following methods, and the results are shown in Table 1 below.

Experimental Example 1: Conversion Rate and Selectivity

The conversion rate of the reactant (isophthalic acid) and the selectivity of 1,3-cyclohexanedicarboxylic acid were measured for the final products obtained in the Examples and Comparative Examples using gas chromatography (GC).

Specifically, the reaction product obtained by the reduction reaction (hydrogenation) of the reactant (isophthalic acid) was diluted with methanol. The diluted solution was analyzed by gas chromatography (GC) to determine the selectivity and conversion rate according to the following Equation. In Equation, each numerical value was converted to a unit of molar ratio (%) and applied.

Selectivity (%)=[(Amount of 1,3-cyclohexanedicarboxylic acid (mol %)/Amount of product(mol %))*100]

Conversion rate (%)=[(Amount of 1,3-cyclohexanedicarboxylic acid added (mol %))−(Amount of 1,3-cyclohexanedicarboxylic acid remaining after reaction (mol %))]/[Amount of 1,3-cyclohexanedicarboxylic acid added (mol %)]*100.

Gas Chromatography (GC) Conditions
1) Column: Agilent 19091J-413 (column length: 30 m, internal diameter: 0.32 mm, film thickness: 0.25 μm)
2) GC system: Gas Chromatography Model Agilent 7890
3) Carrier Gas: Helium
4) Detector: Flame Ionization Detector (FID)

TABLE 1

Results of Experimental Example of Examples and Comparative Examples

| Category | Reactants (wt % in reaction system) isophthalic acid | Catalyst Pd/Cu (wt % in supported catalyst) | Support | (wt % in reaction system) | Conversion rate (%) | Selectivity (%) |
| --- | --- | --- | --- | --- | --- | --- |
| Example 1 | 5 | 1/0.2 | silica | 2 | 92.7 | 93.7 |
| Example 2 | 15 | 1/0.2 | silica | 2 | 55.7 | 94.1 |
| Example 3 | 15 | — | silica | 2 | 1 time-50.2<br>2 times-48.3<br>3 times-48.8 | 1 time-93.4<br>2 times-92.2<br>3 times-87.1 |
| Comparative Example 1 | 5 | 1/0 | silica | 2 | 98.4 | 97.1 |
| Comparative Example 2 | 5 | 1/0.6 | silica | 2 | 61.7 | 94.5 |
| Comparative Example 3 | 15 | 1/0 | silica | 2 | 60.6 | 94.5 |
| Comparative Example 4 | 15 | — | silica | 2 | 1 time-60.1<br>2 times-59.6<br>3 times-41.4 | 1 time-92.4<br>2 times-90.9<br>3 times-92.1 |

From the results in Table 1, it can be seen that the palladium-copper composite metal catalyst of Example 1, had equivalent levels of conversion rate and selectivity as compared with the palladium catalysts of Comparative Examples 1 and 2.

However, it can be confirmed that in Examples 2 and 3 in which catalyst deactivation was accelerated, the initial conversion rate was 55.7%, and while repeating 3 times, the lowest conversion rate was 48.3% and the extent of decrease of the conversion rate was about 7%, whereas in the case of Comparative Examples 3 and 4 using the palladium catalyst, the initial conversion was 60.6%%, and while repeating 3 times, the lowest conversion rate was 41.4% and the extent of decrease of the conversion rate increased rapidly to about 20%, That is, it can be confirmed that when the palladium-copper composite metal catalysts of Examples were used, even during repetitive reactions under non-accelerated conditions, rapid reduction of reaction conversion rate can be prevented due to maintenance of activity due to improvement of acid resistance of the catalyst.

The invention claimed is:

1. A method for preparing 1,3-cyclohexanedicarboxylic acid comprising: reducing isophthalic acid in the presence of a metal catalyst fixed to a silica support and containing a palladium (Pd) compound and a copper (Cu) compound in a weight ratio of 1:0.1 to 0.5.

2. The method for preparing 1,3-cyclohexanedicarboxylic acid of claim 1, wherein the silica support contained in the metal catalyst has a specific surface area of 100 m$^2$/g to 500 m$^2$/g.

3. The method for preparing 1,3-cyclohexanedicarboxylic acid of claim 1, wherein the total pore volume of the silica support contained in the metal catalyst is be 0.5 cm$^3$/g to 2 cm$^3$/g.

4. The method for preparing 1,3-cyclohexanedicarboxylic acid of claim 1, wherein the average pore diameter of the silica support contained in the metal catalyst is 80 Å to 200 Å.

5. The method for preparing 1,3-cyclohexanedicarboxylic acid of claim 1, wherein the metal catalyst includes 0.1% to 10% by weight of the palladium (Pd) compound relative to the silica support.

6. The method for preparing 1,3-cyclohexanedicarboxylic acid of claim 1, wherein the step of reducing isophthalic acid includes contacting the isophthalic acid with hydrogen gas.

7. The method for preparing 1,3-cyclohexanedicarboxylic acid of claim 1, wherein the step of reducing isophthalic acid is carried out at 50° C. to 350° C.

8. The method for preparing 1,3-cyclohexanedicarboxylic acid of claim 1, wherein the step of reducing isophthalic acid is carried out under a pressure of 30 bar to 150 bar.

9. The method for preparing 1,3-cyclohexanedicarboxylic acid of claim 1, wherein the metal catalyst is used in an amount of 10 to 80 parts by weight relative to 100 parts by weight of the isophthalic acid.

10. The method for preparing 1,3-cyclohexanedicarboxylic acid of claim 1, wherein the metal catalyst includes a palladium (Pd) compound and a copper (Cu) compound in a weight ratio of 1:0.3 to 0.5.

11. The method for preparing 1,3-cyclohexanedicarboxylic acid of claim 1, wherein a selectivity defined by the following Equation 1 is 90% or more:

Selectivity (%)=[(Amount of 1,3-cyclohexanedicarboxylic acid (mol %)/Amount (mol %) of product)*100]. [Equation 1]

12. The method for preparing 1,3-cyclohexanedicarboxylic acid of claim 1, wherein after a step of reducing isophthalic acid in the presence of a metal catalyst fixed to a silica support and containing a palladium (Pd) compound and a copper (Cu) compound in a weight ratio of 1:0.1 to 0.5, the method further comprises a step of recovering the metal catalyst; and a step of reducing the isophthalic acid in the presence of the recovered metal catalyst.

13. The method for preparing 1,3-cyclohexanedicarboxylic acid of claim 12, wherein the step of recovering the metal catalyst; and the step of reducing the isophthalic acid in the presence of the recovered metal catalyst are repeatedly carried out twice or more.

14. The method for preparing 1,3-cyclohexanedicarboxylic acid of claim 12, wherein in the step of reducing the isophthalic acid in the presence of the recovered metal catalyst, the conversion rate defined by the following Equation 2 is 45% or more:

Conversion rate (%)=[(Amount of 1,3-cyclohexanedicarboxylic acid added (mol %))−(Amount of 1,3-cyclohexanedicarboxylic acid remaining after reaction (mol %))]/[Amount of 1,3-cyclohexanedicarboxylic acid added (mol %)]*100. [Equation 2]

* * * * *